United States Patent
Friedmann (10) Patent No.: US 8,962,309 B2
(45) Date of Patent: Feb. 24, 2015

(54) APPARATUS AND PROCESS FOR THE CONVERSION INTO BIOGAS OF FERMENTATION STILLAGE ARISING AS A WASTE PRODUCT OF ETHANOL PRODUCTION

(75) Inventor: Hans Friedmann, Scheyern-Fernhag (DE)

(73) Assignee: Agraferm Technologies AG, Pfaffenhofen/ILM (DE)

(*) Notice: Subject to any disclaimer, the term of this patent is extended or adjusted under 35 U.S.C. 154(b) by 1108 days.

(21) Appl. No.: 12/336,571

(22) Filed: Dec. 17, 2008

(65) Prior Publication Data

US 2009/0176289 A1    Jul. 9, 2009

Related U.S. Application Data

(60) Provisional application No. 61/014,862, filed on Dec. 19, 2007.

(30) Foreign Application Priority Data

Dec. 19, 2007    (DE) .......................... 10 2007 061 137

(51) Int. Cl.
  *C12M 1/00*    (2006.01)
  *C12M 3/00*    (2006.01)
  (Continued)

(52) U.S. Cl.
  CPC ............... *C12P 5/023* (2013.01); *C12M 21/04* (2013.01); *C12M 21/12* (2013.01); *C12M 23/44* (2013.01);
  (Continued)

(58) Field of Classification Search
  CPC ...... C12M 21/04; C12M 21/12; C12M 23/44; C12M 27/20; C12M 29/24; C12M 47/18

USPC ............... 435/289.1, 294.1, 303.1, 304.1, 41, 435/161, 162
  See application file for complete search history.

(56) References Cited

U.S. PATENT DOCUMENTS

2,595,827 A    5/1952    Boruff et al.
5,177,009 A    1/1993    Kampen
  (Continued)

FOREIGN PATENT DOCUMENTS

DE    3035683 A1    4/1982
DE    246531 A1    6/1987
  (Continued)

OTHER PUBLICATIONS

German Office Action dated Jul. 8, 2011, eight pages.
  (Continued)

*Primary Examiner* — Nathan Bowers
(74) *Attorney, Agent, or Firm* — Rankin, Hill & Clark LLP (57) ABSTRACT

The invention relates to an apparatus for the conversion into biogas of fermentation stillage arising as a waste product of ethanol production. This apparatus comprises a separation unit for the separation of the fermentation stillage into a thin fraction and a thick fraction, at least one biogas reactor for fermenting the thin fraction and/or the thick fraction, and a storage tank. According to a first aspect of the present invention, two biogas reactors are provided, to separate the thin fraction and the thick fraction independently of one another. According to a second aspect of the present invention, a nitrogen sink is provided downstream of the storage tank to provide, from the reactor effluent, process water with low or no nitrogen content which may then be fed to the reactor and/or the bioethanol plant. According to a third aspect the invention is characterized by a combination of a single-stage separation unit and a heavy-duty biogas reactor with a pore-free flow path.

30 Claims, 6 Drawing Sheets

(51) Int. Cl.
*C12P 7/06* (2006.01)
*C12P 5/02* (2006.01)
*C12M 1/107* (2006.01)

(52) U.S. Cl.
CPC ............... *C12M 27/20* (2013.01); *C12M 29/24* (2013.01); *C12M 47/18* (2013.01); *Y02E 50/17* (2013.01); *Y02E 50/343* (2013.01)
USPC .................. 435/294.1; 435/289.1; 435/303.1; 435/304.1; 435/41; 435/161; 435/162

(56) References Cited

U.S. PATENT DOCUMENTS

| | | | |
|---|---|---|---|
| 5,250,182 | A | 10/1993 | Bento et al. |
| 2002/0079266 | A1* | 6/2002 | Ainsworth et al. ........... 210/603 |
| 2002/0124613 | A1 | 9/2002 | Sower |
| 2003/0121851 | A1 | 7/2003 | Lee, Jr. |
| 2004/0037933 | A1* | 2/2004 | Rieke et al. .................... 426/465 |
| 2005/0153410 | A1 | 7/2005 | Hallberg et al. |
| 2006/0041153 | A1 | 2/2006 | Cantrell et al. |
| 2006/0194296 | A1 | 8/2006 | Hammond et al. |
| 2007/0141691 | A1* | 6/2007 | Hirl ................................ 435/161 |
| 2007/0254089 | A1 | 11/2007 | Hickey et al. |
| 2008/0248519 | A1 | 10/2008 | Friedmann et al. |

FOREIGN PATENT DOCUMENTS

| | | |
|---|---|---|
| DE | 4213015 | 10/1993 |
| DE | 19655101 A1 | 10/1999 |
| DE | 19947339 A1 | 4/2001 |
| DE | 10005114 A1 | 8/2001 |
| DE | 10321607 | 12/2004 |
| EP | 1757562 A1 | 2/2007 |
| EP | 1790732 | 5/2007 |
| WO | 2006/021087 A1 | 3/2006 |
| WO | 2006/029971 A2 | 3/2006 |
| WO | WO-2006042551 A1 * | 4/2006 |
| WO | 2007/025739 | 3/2007 |

OTHER PUBLICATIONS

Computer English Translation of DE19655101 published Oct. 28, 1999, nine pages.
Computer English Translation of EP 1757562 published Feb. 28, 2007, fifty-two pages.
Computer English Translation of DE 10005114 published Aug. 16, 2001, seventeen pages.
Computer English Translation of DE 19947339 published Apr. 12, 2001, thirty-eight pages.
English Abstract of DE 4213015 published Oct. 28, 1993, Applicant—Maerkl, Herbert, two pages.
English Abstract of DE 10321607 published Dec. 2, 2004, Applicant—Messo Chemietechnik GmbH, one page.

* cited by examiner

FIG. 1

| | flow [-] | fermenter [t/h] | organic dry weight [t/h] | organic dry weight-% [kg/kg] | N [t/h] | NH4-N [t/h] | TN [kg/kg] | NH4-N [kg/kg] | retention time [d] | reactor volume [m³] | loading rate [kg/(m³·d)] |
|---|---|---|---|---|---|---|---|---|---|---|---|
| Fermentation stillage | 9.1 | 100,00 | 10,00 | 10% | 1,00 | 0,00 | 0,010 | 0,000 | | | |
| Thin fraction | 9.3 | 80,00 | 5,00 | 6% | 0,50 | 0,00 | 0,006 | 0,000 | | | |
| PW heavy-duty biogas reactor | 9.5 | 5,00 | 0,00 | 0% | 0,00 | 0,00 | 0,000 | 0,000 | | | |
| Input heavy-duty biogas reactor | 9.6 | 85,00 | 5,00 | 6% | 0,50 | 0,00 | 0,006 | 0,000 | 2,94 | 6000 | 20 |
| Gas heavy-duty biogas reactor | 9.9 | 4,25 | 4,25 | 100% | 0,00 | 0,00 | 0,000 | 0,000 | | | |
| Effluent heavy-duty biogas reactor | 9.7 | 80,75 | 1,60 | 2% | 0,50 | 0,43 | 0,006 | 0,005 | | | |
| Thick fraction | | 20,00 | 5,00 | 25% | 0,50 | 0,00 | 0,025 | 0,000 | | | |
| PW thick sludge fermenter | 9.12 | 30,00 | 0,00 | 0% | 0,00 | 0,00 | 0,000 | 0,000 | | | |
| Input thick sludge fermenter | 9.13 | 50,00 | 5,00 | 10% | 0,50 | 0,00 | 0,010 | 0,000 | 16,67 | 20000 | 6 |
| Gas thick sludge fermenter | 9.15 | 3,75 | 3,75 | 100% | 0,00 | 0,00 | 0,000 | 0,000 | | | |
| Effluent thick sludge fermenter | 9.16 | 46,25 | 2,00 | 4% | 0,50 | 0,33 | 0,011 | 0,007 | | | |
| Total effluent | 9.18 | 127,00 | 3,60 | 3% | 1,00 | 0,75 | 0,008 | 0,006 | | | |
| Gas flow | 9.28 | 0,50 | 0,00 | 0% | 0,50 | 0,50 | 1,000 | 1,000 | | | |
| Solid fertiliser | 9.20 | 6,69 | 2,34 | 35% | 0,18 | 0,01 | 0,026 | 0,002 | | | |
| Liquid effluent | 9.21 | 120,31 | 1,26 | 1% | 0,32 | 0,24 | 0,003 | 0,002 | | | |
| Process water | 9.26 | 112,16 | 0,11 | 0% | 0,01 | 0,01 | 0,000 | 0,000 | | | |
| Concentrate | | 7,65 | 1,15 | 15% | 0,31 | 0,23 | 0,041 | 0,029 | | | |
| Liquid fertiliser | 9.25 | 8,15 | 1,15 | 15% | 0,81 | 0,73 | 0,100 | 0,089 | | | |

| | |
|---|---|
| Thin fraction degradability | 85% |
| Thick fraction degradability | 75% |

APPARATUS AND PROCESS FOR THE CONVERSION INTO BIOGAS OF FERMENTATION STILLAGE ARISING AS A WASTE PRODUCT OF ETHANOL PRODUCTION

The present Invention relates to an apparatus and a process for the conversion into biogas of fermentation stillage arising as a waste product of ethanol production.

Known from EP 1 790 732 A1 is a method and an apparatus for the recycling of fermentation stillage in alcohol production. In this process, insoluble components are removed from the unprocessed fermentation stillage by centrifuging. In the second stage of separation, finely distributed components are separated from the liquid fraction by air flotation, centrifuging, vacuum filtration or a combination of these processes. Thickened dense fractions (thick stillage) from both these separation stages have a low salt content and are further processed into feed with high nutritional value. Liquid fractions (thin stillage) from both separation stages are mixed under controlled conditions and acidified until a pH value of between 4.8 and 9.2 is obtained. They are then fed into an anaerobic heavy-duty biogas reactor together with biomass, for an anaerobic digestion process. The biomass is comprised of acetogen and methanogen bacteria, with the anaerobic digestion being carried out at temperatures of between 25° C. and 40° C. The loading rates of the mesophilic anaerobic heavy-duty fermenter are between 3 and 70 $kg_{oTM}/m^3$ d). The accumulated thick stillage is removed and dried. Biogas given off from the fermenter is biologically desulphurised, with elementary sulphur obtained as a by-product. The biogas is then used for energy. Next, the nitrogenous elements are separated from the liquid fractions. The liquid fractions then receive aerobic treatment in which the solids are separated off. After concentration, the solids may be used in agriculture as fertiliser. After distillation, any resulting process water may be used in the further process.

Described in US 2007/0141691 is a process and an apparatus for ethanol production. The process provides for the conversion of fermentation stillage into biogas by means of anaerobic digestion processes. The biogas is then used instead of natural gas in ethanol production or for power generation. The anaerobic digestion process of the total fermentation stillage should be able to generate more methane than natural gas in the production of ethanol. The total fermentation stillage, anaerobic digested sludge and reconditioned water are mechanically mixed to produce a liquid manure mixture. The liquid manure is brought from a holding tank into an anaerobic plug flow fermenter or plug flow reactor. The digested sludge is mixed mechanically in a plug flow fermenter or by the introduction of biogas. The anaerobic plug flow fermenter is heated by the heat from combustion of the biogas. The biogas is used in an internal combustion engine for power generation and as fuel for a boiler for steam generation. The electricity is used to operate mechanical systems in the ethanol production unit and the anaerobic digestion system. The steam from the boiler is used for the production of ethanol. The waste heat of a heat exchanger of the internal combustion engine and the exhaust gas of the combustion engine are used by a fresh water cooling system. The fresh water is used to heat the anaerobic digestion tank. The mixed fermentation stillage is transferred from the biogas reactor to a screw press, for separation of the solid from the liquid digested material. The solid digested material is dewatered and used as fertiliser. The ammonium is removed from the liquid digested material. The resulting ammonium solution is also used as fertiliser. In addition to the fermentation stillage used, a dung flow and a washing water flow from a milking unit are also needed as extra feed materials. In one embodiment, the total flow of 25 t/h is mixed with a separator outflow and fed into a plug flow fermenter. For a retention time of between 15 and 20 days, a reactor volume of 70,250 $m^3$ is required. The resultant loading is 2.69 kg ($m^3$ d). The biogas flow is 12.7 t per day. In the biogas reactor there is an $NH_4$—N concentration of 9 g/kg, which leads to a marked inhibition of the methane bacteria. Stable operation of the fermenter is therefore possible only with intensive process monitoring. The digested sludge separation is carried out with an efficiency of 75%. There is a solid discharge flow of 16.9 t/h (35% of the total solids content) and a liquid flow of 150.4 t/h (1.3% of the total solids content), of which 25 t/h are returned to the biogas reactor as process water. With an $NH_4$—N content of 9 g/kg, this process water flow contributes to the high $NH_4$—N concentration in the reactor, which has a harmful and/or inhibiting effect on reactions.

Described in US 2006/0194296 A1 is the separation of stillage by means of a centrifuge. This involves splitting into various fractions by means of micro-filtration and ultra-filtration. The fractions are dried and sold as "value-added product".

US 2006/0041153 A1 describes the separation of an oil flow from evaporated thin stillage. In this process, DDGS (Dried Distiller's Grain with solubles) is produced.

Described in US 2005/0153410 A1 is the production of DDGS. This involves the production of biogas from dung. In addition, the biogas is burned to cover the heat requirements of the bioethanol plant.

In U.S. Pat. No. 5,250,182, the membrane separation of thin stillage by means of micro-filtration, ultra-filtration and reverse osmosis is described. This involves the separating off of lactic acid and glycerol. The resulting water is purified to process water quality and returned to the ethanol process. The different filtration steps are executed using membranes. In this process, the use of a conventional evaporator in the ethanol production is made unnecessary by the membrane filtration.

U.S. Pat. No. 5,177,009 discloses a process for ethanol production and the recovery of by-products such as e.g. glycerol. In this process, the stillage is separated by centrifuging. The solids are dried and processed into feed and DDGS. Individual components are dissolved out of the thin stillage by means of various process steps.

Known from U.S. Pat. No. 2,595,827 is a further process for alcohol production in which the stillage is split up into various components by means of a screen and a centrifuge.

DE 42 13 015 A1 describes a biogas reactor. In the biogas reactor, reactor zones are formed in different reactors by means of separating elements. The separating elements are in the form of flat panels inclined downwards, each forming—with the reactor wall of the reactor housing—a gas collecting space. In the gas collecting space, the biogas rising up from the reactor zones lying below is impounded. If all the biogas collected is removed from the gas space via a pipe with a valve, then above this separating element a zone with little gas is created, which encourages the sedimentation of biogas. If then the valve is closed, biogas flows across at an outer overflow edge of the separating element into the space of the next reactor zone lying above. Since the outflowing biogas rises on one side only in one half of the space, a circulating flow which promotes thorough mixing occurs. The rate of the circulating flow rises as the gas flow volume increases. Through the removal of different gas flow volumes and adjustment of the valves, the circulating flow may be set so that on the one hand adequate mixing is achieved, while on the other hand the removal of active biomass is avoided.

DE 100 05 114 A1 discloses a process for biomass retention in biogas reactor, and an apparatus for conducting the process. The process may be used in particular in aerobic sludge bed digesters. Here the outlet of the biogas reactor is supplied with pressure, so that with increased pressure, sedimentation of the biomass may be effected. The apparatus has a biogas reactor connected via a pipe to a solids separator, which here is a flooded solids separator. The process is applicable in particular to anaerobic reactors. The biogas reactor has a tower-like reactor structure, to which effluent is fed in via a pipe at the bottom end of the biogas reactor, and then flows through the biogas reactor from bottom to top, during which the effluent is purified. The purified water may then flow out over an overflow at the top of the biogas reactor. The anaerobic decomposition of organic substances in the effluent produces biogas, comprised mainly of methane and carbon dioxide. Small amounts of other gases may also be formed, for example hydrogen sulphide or ammonia. To avoid any gas accumulation in the upper section of the biogas reactor, it is provided with further gas collecting facilities which collect the biogas formed, so that it may be drawn off via valves and a gas collection pipe.

In WO 2007/025739, an agitator for a fermenter is described. The agitator has an agitator shaft, which stands roughly vertical in the fermenter. By this means the substrate found in the fermenter is circulated in horizontal planes. This permits the setting of several layered decomposition zones.

DE 103 21 607 A1 discloses a process for the production of bioethanol. In this process, provision is made in the preliminary stages to remove the gluten from grain (rye, wheat). In this case it is possible to design a thick sludge fermenter for a high solids concentration.

WO 2006/021087 discloses a process for the production of ethanol, wherein either the complete fermentation stillage or only the thin stillage are anaerobically digested to biogas.

US 2007/0254089 A1 discloses a process for the production of ethanol, wherein only the thin stillage is anaerobically digested thereafter.

WO 2006/029971 A2 and DE 30 35 683 disclose processes for the production of ethanol, wherein only the thick stillage is anaerobically digested thereafter.

Besides, DD 246 531 describes an anaerobic digestion of slurry for the production of methane, wherein the liquid phase of a mixed liquid/solid substrate composition is digested in a first bioreactor and, thereafter, the solid remains of the digestion in the first bioreactor are digested in a second bioreactor downstream of the first bioreactor.

The drawback with the processes known from the prior art is that the ethanol plants may not be operated efficiently and with energy self-sufficiency, and require a relative large reactor volume.

The invention is based on the problem of creating an apparatus and a process for ethanol production with which such ethanol plants may be operated efficiently.

The problem is solved by an apparatus as disclosed herein, and a process as disclosed herein. Further advantageous developments are also described herein.

According to a first aspect, the present invention comprises, for the conversion into biogas of fermentation stillage arising as a waste product of ethanol production
- a separation unit for the separation of the fermentation stillage into a thin fraction and a thick fraction, wherein the thin fraction has a lesser dry weight content than the thick fraction
- at least two biogas reactors, wherein the first biogas reactor is designed to ferment the thin fraction, and is subsequently referred to as the thin sludge fermenter, and the second biogas reactor is designed to ferment the thick fraction, and is subsequently termed the thick sludge fermenter, and
- a storage tank for collection of the biogas produced in the fermenter and the reactor effluent.

Due to the fact that the fermentation stillage is split into a thin and a thick fraction, the thin fraction can be fermented independently of the thick fraction. The thin fraction contains a high proportion of soluble solids and no insoluble solids or else only a very small amount. The thin fraction preferably has a dry weight content (total solids) up to approx. 20%, most preferably of approx. 5 to 15%. The thick fraction preferably has a dry weight of at least 20%, most preferably of approx. 20 to 40%. In a preferred embodiment of the invention the dry weight content of the thin fraction is at least two times, most preferred three times, lower than that of the thick fraction. Through the provision of two reactors, each geared to their content, the thin fraction may be converted with a high throughput, and the thick fraction independently of the former with the necessary retention time and correspondingly lower throughput. Since the thin fraction is converted rapidly into biogas, a reactor with very low volume is sufficient. This reduces the energy needed for controlling the reactor temperature, and makes the whole process very efficient in terms of energy. In addition, in comparison with conventional apparatus, an altogether smaller reactor volume is needed for the same throughput. Also a lower temperature is sufficient in the fermenters, bringing a further rise in energy efficiency.

According to a second aspect of the present invention, the apparatus for the conversion into biogas of fermentation stillage arising as a waste product of ethanol production comprises:
- a biogas reactor for fermentation of the fermentation stillage
- a storage tank for collection of the biogas produced in the fermenter and the reactor effluent
- a separation unit, to provide from the reactor effluent process water with few nitrogenous compounds and a fraction with many nitrogenous compounds, with this separation unit being described below as the nitrogen sink, and
- a return pipe from the unit into the biogas reactor and/or into a reactor for ethanol fermentation, to use the process water for dilution of the respective reactor content.

In the nitrogen sink, a low-nitrogen process water flow is produced from the reactor effluent. By this means it is possible to direct the low-nitrogen process water flow back into the biogas reactor and/or into the reactor for ethanol fermentation, in order to dilute the reactor contents without at the same time increasing the pH value. On the one hand this saves the costs of fresh process water while on the other hand it avoids the concentration of too much ammonia in the reactor, since ammonia is toxic to the micro-organisms in the reactor. It is also possible to have a higher loading rate than in the case of the prior art, since the biogas reactor operates more efficiently. A smaller reactor volume may therefore be provided, which reduces the energy needed for temperature control of the biogas reactor and makes the whole process very energy-efficient. In comparison with conventional apparatus, an altogether smaller reactor volume is required for the same throughput.

Due to the high loading rates and the reduced reactor volume, the energy requirement of the apparatus according to the invention is so low that the amount of biogas produced is sufficient to meet the thermal and electrical energy requirement for production of the biogas and the ethanol.

According to a further aspect of the present invention, an apparatus is provided for the conversion into biogas of fermentation stillage arising as a waste product of ethanol production which comprises a separation unit for the separation of the fermentation stillage into a thin fraction and a thick fraction, wherein the thin fraction has a lesser dry weight content than the thick fraction. The apparatus also has at least one biogas reactor, to ferment at least the thin fraction. The thin fraction preferably has a dry weight content (total solids) up to approx. 20%, most preferably of approx. 5 to 15%. The thick fraction preferably has a dry weight of at least 20%, most preferably of approx. 20 to 40%. In a preferred embodiment of the invention the dry weight content of the thin fraction is at least two times, most preferred three times, lower than that of the thick fraction. This apparatus is distinguished by the fact that the separation unit, which is preferably a decanting centrifuge, is a single-stage unit, i.e. only a single separation mechanism is used to split the fermentation stillage into the thin fraction and the thick fraction. The biogas reactor is a heavy-duty (high performance) biogas reactor through which the thin fraction flows, while, preferably, the flow path in the biogas reactor is pore-free. This makes it possible for the thin fraction too to contain a certain proportion of solids, so that it may be reliably fermented for some time in the reactor. A heavy-duty (high-performance) biogas reactor according to the invention is a reactor for a biogas fermentation for which the hydraulic retention time and/or volumetric organic load is adjusted such that the fermentation process cannot be run stable without further steps. A biogas fermentation cannot be run stable without further steps, for example, when the volumetric organic load is above approx. 8 $kg_{oTM}/(m^3d)$ and/or the hydraulic retention time is less than seven days. In an embodiment of the invention the ratio of diameter:height of the heavy duty biogas reactor is from approx. 1:3 to 1:1.

This combination of a single-stage separation unit and heavy-duty biogas reactor with pore-free flow path is extremely efficient, since a high throughput may be obtained with a relatively small, cost-effective plant. It is also very easily constructed and able to be operated reliably. The thick fraction may be fermented in another reactor. Therefore, it is alternatively possible to process the thick fraction in a different manner. In particular the thick fraction may not be subjected to an anaerobic digestion in a thick sludge biogas fermenter but, depending on the composition of the fermentation stillage, may be used as solid fertiliser, either with or without further processing.

The invention is explained by an example and with the aid of the drawing, which shows in:

FIG. 2 a mass balance of an exemplary embodiment of the process according to the invention FIG. 3 an embodiment of a thin sludge fermenter, FIG. 4 a detail of a thick sludge fermenter with an eccentrically mounted agitator in cross-section, FIG. 5 a diagram of a fermentation of thin wheat stillage in a 9 $m^3$ thin sludge fermenter showing the methane yield, acetic acid equivalent and loading rate.

Figure 1:
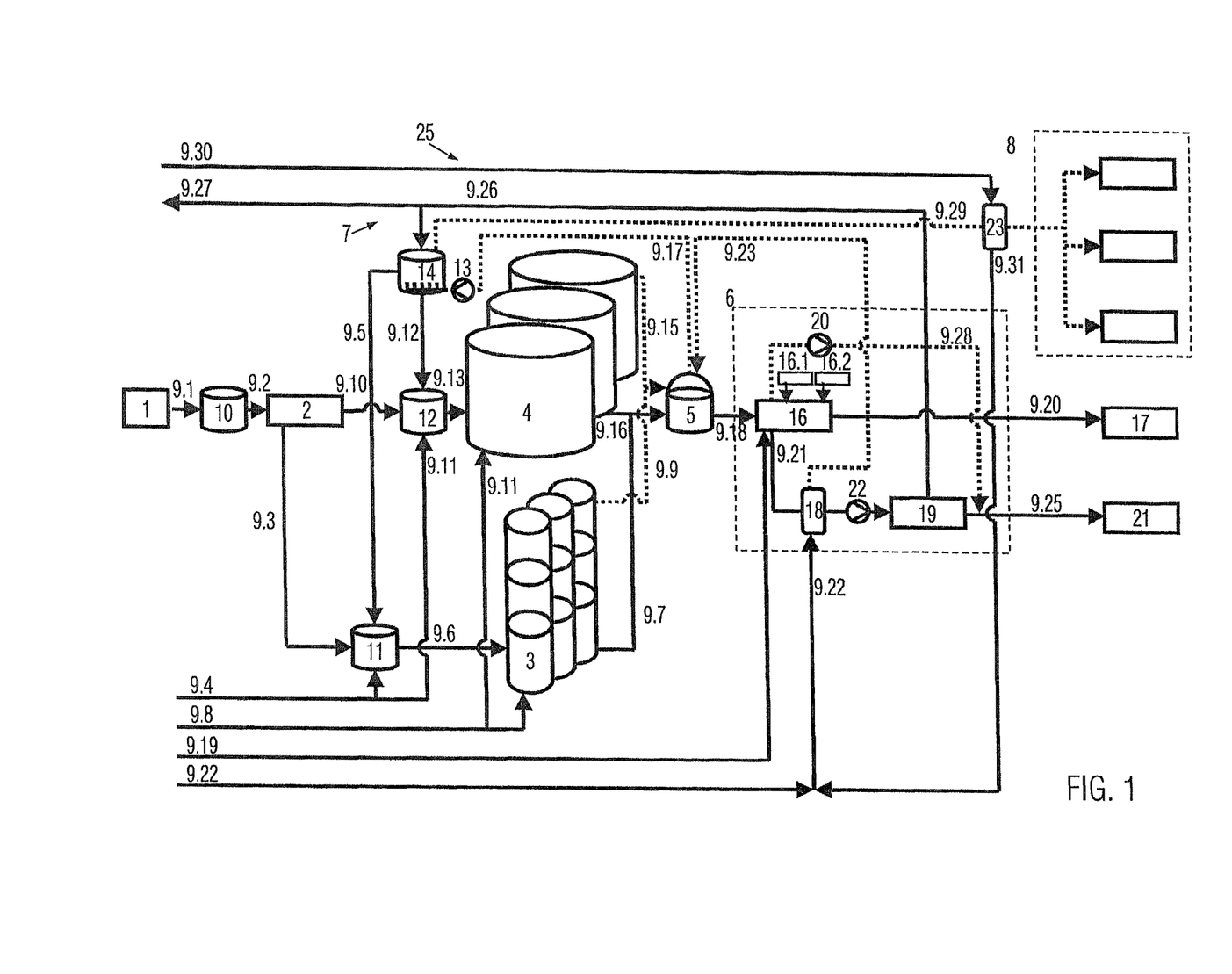
FIG. 1 the structure of an apparatus according to the invention

In one embodiment of the invention the apparatus according to the invention is a biogas plant 25. The biogas plant 25 converts into biogas, fermentation stillage arising as a waste product of ethanol production in the bioethanol plant 1. The biogas plant 25 has a separation unit 2, a thin sludge fermenter 3, a thick sludge fermenter 4, a storage tank 5, a nitrogen sink 6, a process water return pipe 7, and a biogas recycling unit 8.

In the separation unit 2, the fermentation stillage from the bioethanol plant 1 is split into a thin fraction and a thick fraction. The thin fraction is fermented in the thin sludge fermenter 3. The thick fraction is fermented in the thick sludge fermenter 4. The reactor effluent from the two fermenters 3, 4 and the biogas generated therein are collected in the storage tank 5. The reactor effluent is separated in the nitrogen sink 6. This involves the provision of low-nitrogen and nitrogen-free process water. The purified process water is fed via the process water return pipe 7 to the bioethanol plant 1 and/or the biogas plant 25. The biogas produced is utilised in the biogas recycling unit 8, to cover the energy requirements of the bioethanol plant 1 and the biogas plant 25.

The bioethanol plant 1 is connected via a pipe section 9.1 to the biogas plant 25 or to a buffer tank 10 of the biogas plant 25. The buffer tank is designed for storage and comparison of the fermentation stillage.

The fermentation stillage emanating from the bioethanol plant 1 has roughly the following properties:
temperature: approx 60° C. to 80° C.
pH value: approx. 3 to 4.5
diluted (dry weight TM 5%-15%)
substances which can be filtered off: approx. 1.5%-5%
nitrogen content: approx. 5%-20% of TM The fermentation stillage comprises C5 and C6 sugars, a protein fraction of the input material, a yeast biomass (thermally deactivated), buffer residues of the enzyme solutions used, undigested fibre and starch residues, small amounts of ethanol and other higher alcohols and mineral salts from the yeast fermentation.

From the buffer tank 10 a pipe section 9.2 leads to the separation unit 2 for the separation of the fermentation stillage into a thin fraction and a thick fraction.

The separation unit 2 is in the form of a decanting centrifuge. The separation unit 2 may also be provided in the form of a membrane filtration unit, a drum filter or a drum screen.

The separation unit 2 is connected to a thin fraction storage tank 11 by a pipe section 9.3 for transferring the thin fraction. A pipe section 9.4 for the introduction of a stillage conditioning agent leads into the thin fraction storage tank 11. The stillage conditioning agent is a mixture of NaOH, $CaCO_3$, MgOH, $H_2O_2$, KCl and a phosphate. Purified process water is fed into the thin fraction storage tank 11 via a pipe section 9.5. In the thin fraction storage tank 11, the thin fraction mixes with the stillage conditioning agent and the process water.

Figure 3:
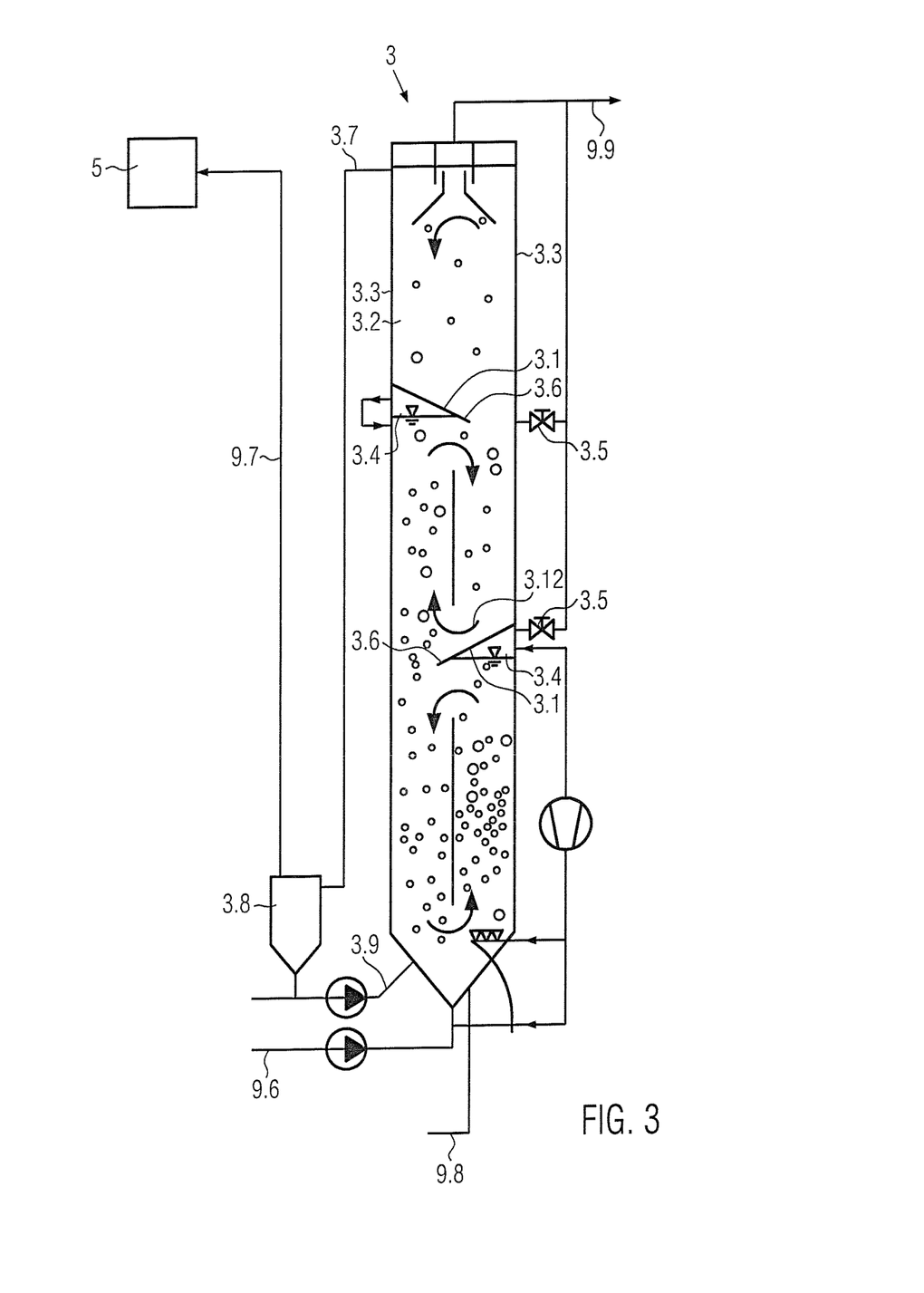

The thin fraction storage tank 11 is connected to the thin sludge fermenter 3 via a pipe section 9.6. Through this pipe section 9.6, the enriched and diluted thin fraction reaches the thin sludge fermenter 3. The thin sludge fermenter 3 is so designed as to provide good thorough mixing of the reactor content and adequate retention of active biomass. The thin sludge fermenter 3 is in the form of a tall biogas reactor in which the base area is very small compared to the height of the reactor (FIG. 3).

In the thin sludge fermenter 3, at different reactor levels, reactor zones 3.2 are formed by separating elements 3.1 arranged offset above one another. The separating elements 3.1 are mounted opposite one another on a reactor wall 3.3, and are in the form of flat plates sloping downwards. The space beneath the separating elements 3.1 forms in each case, together with the reactor wall 3.3, a gas collecting space 3.4. The biogas rising from the reactor zone 3.2 lying below in each case is stored in the gas collecting spaces 3.4. Located in the upper part of the gas collecting spaces 3.4 are valves 3.5. Biogas produced in the reactor may be removed via the valves 3.5. In this way a gas-deficient zone is created above the separating elements 3.1, which encourages the sedimentation of biogas. Overflow edges 3.6 are formed at the radially inwards facing ends of the separating elements 3.1.

When a valve 3.5 is closed, biogas flows over the overflow edge 3.6 of the separating element 3.1 into the space of the next reactor zone 3.2 lying above. Since the overflowing biogas rises on one side only into one half of the space, a circulating flow promoting thorough mixing occurs. The rate of circulating flow increases as the volume of gas flowing rises. By removing different gas flow volumes through adjustment of the valves 3.5, the circulating flow may be set so that on the one hand adequate mixing occurs, while on the other hand the discharge of active biomass is avoided.

The division of the thin sludge fermenter 3 into reactor zones 3.2, and the biomass retention obtained thereby, correspond to the reactor of DE 42 13 015 A1 to which reference is made in full.

Provided at the upper end section of the thin sludge fermenter 3 is a pipe section 3.7, via which the thin sludge fermenter is connected to the upper end section of a solids separator 3.8. Via a pipe section 3.9 the lower section of the solids separator is connected to the lower section of the thin sludge fermenter 3. Provided as solids separator 3.8 is in particular a solids separator dammed at the top. Due to its downwards offset layout, the solids separator 3.8 is dammed from above against the outflow of the thin sludge fermenter 3. In the solids separator, the outgassing of biogas is avoided by the pressure generated by the above layout. Active biogas is removed from the reactor effluent and fed back into the thin sludge fermenter 3 via pipe section 3.9. This raises the pressure in the thin sludge fermenter 3. The pressure causes evolved biogas to turn into a solution, so that sedimentation of the biomass may be effected and any flushing out of the biomass over the biogas generated may be prevented.

The design of the thin sludge fermenter 3 corresponds to the biomass retention according to DE 100 05 114 A1, which content is fully incorporated herewith.

Provided at the solids separator 3.8 is a pipe section 9.7 which connects the solids separator with the storage tank 5. The pipe section 9.7 ends at roughly the height of the connection of the pipe section 3.7 to the thin sludge fermenter, so as to set the pressure in the pipe section 9.7 such that the reactor outflow is more or less unpressurised.

Via a pipe section 9.8, a mineral trace element solution can be fed into the thin sludge fermenter 3. The pipe section 9.7 leads into the storage tank 5. The valves 3.5 are connected to the storage tank 5 via a common pipe section 9.9. The biogas generated in the thin sludge fermenter 3 is fed into the storage tank 5 through the pipe section 9.9.

The trace elements of the trace element solution, also described as trace metals or micro-nutrients, may include iron (Fe), nickel (Ni), cobalt (Co), selenium (Se), tungsten (W), lead (Pb), copper (Cu), cadmium (Cd), molybdenum (Mo), tungsten (W), vanadium (V), manganese (Mn), boron (B) and zinc (Zn). The trace element solution comprises at least one of these elements. The composition of the trace element solution and the amount of each element are dependent on the substrate used and the micro-organisms of the fermentation involved. For biogas processes the trace element solution preferably contains at least molybdenum, selenium, cobalt and boron. This latter trace element solution is beneficial especially for maize substrates. In biogas processes, molybdenum, nickel, selenium and cobalt may be added to the fermenter in relative high concentrations, and significantly improve the performance and efficiency of the fermentation.

In addition to at least one but preferably several trace elements, the solution comprises at least one but especially preferably two or more complexing agents with different complexing constant or affinities to the various metal ions. Complexing agents are compounds suitable for the complexing and masking of metals. They are also known by the description of "chelating agents". Complexing occurs through a coordinative bonding between the metal atom and one or more molecules of the complexing agent surrounding the metal atom. The complexing constants of the complexing agent should be high enough to maintain the respective trace elements of the solution in solution form in the presence of sulphide ions in the fermenter, taking into account the pH value, plus the dissociation constants of the complexing agent and of the $H_2S$.

The complexing agents used are resorbed by micro-organisms, preferably anaerobic bacteria, with (1) the trace elements being transported in complexed form across the cell membrane, whereupon (2) the trace elements are released in the cell. The latter may be effected by a consequent reaction of the complexing agent, by oxidation or reduction of the trace element, by the pH shift on crossing the cell wall, or through the biological decomposition of the complexing agent. In the case of a bacterial process, such as the biogas process, the transport of the trace element in complexed form is effected across the bacterial cell wall and the cell membrane into the cytosol of the cell, where the trace element is released.

Suitable complexing agents are known and to some extent available commercially. Examples of preferred complexing agents according to the invention are oxocarboxylic acids, for example β-oxocarboxylic acids such as acetoacetate or α-oxocarboxylic acids such as pyruvic acid and their respective salts; acetylacetone; orotic acid; simple amino acids, for example alanine, valine, cystine, phenylalanine, aspartic acid, glutamic acid, leucine, threonine, tryphtophane or glycine, and also ortho-, meta- and para-isomers of the tyrosines; dipeptide, tripeptide; polymethine dyes such as for example catechol (also known as catechin); citric acid and its salts, iso-citric acid and its salts; salicylic acid; chelate complexing agents such as for example diethylenetriaminepentaacetic acid (DTPA), hydroxyethylenediaminetriacetic acid (HEDTA), ethylenediaminedisuccinic acid (EDDS), ethylenediiminodiacetic acid (EDDA), ethylenediamenetetraacetic acid (EDTA), nitrilotriacetic acid (NTA); dicarboxylic acids such as for example malonic acid, tartaric acid, malic acid, meso-malic acid or oxalic acid and their salts; hydroxycarboxylic acids such as for example the lactic acids and their salts; modified cyclodextran; galactonic acid; mercaptoacetic acid (thioglycolic acid), mercaptoproprionic acid (thiolactic acid), mercaptomalic acid, thiodiacetic acid, boric acid, phosphorus acid, salts of phosphorus acid such as (hydroxy-) phosphonate, phosphoric acid, salts of phosphoric acid such as (hydroxy-)phosphate, oligopeptides such as the iron-bonding siderophores such as enterochelin, and zeolites.

A trace element solution of this kind contributes to a further increase in the efficient of biogas generation.

In the embodiment of the invention according to FIG. 1 the separation unit 2 is connected via a pipe section 9.10 to a thick fraction storage tank 12. Over a pipe section 9.11 branching off from the pipe section 9.4, stillage conditioning agent is fed into the thick fraction storage tank 12. Process water is fed into the thick fraction storage tank through a pipe section 9.12. The diluted and enriched thick fraction reaches the thick sludge fermenter 4 via a pipe section 9.13.

Figure 4:
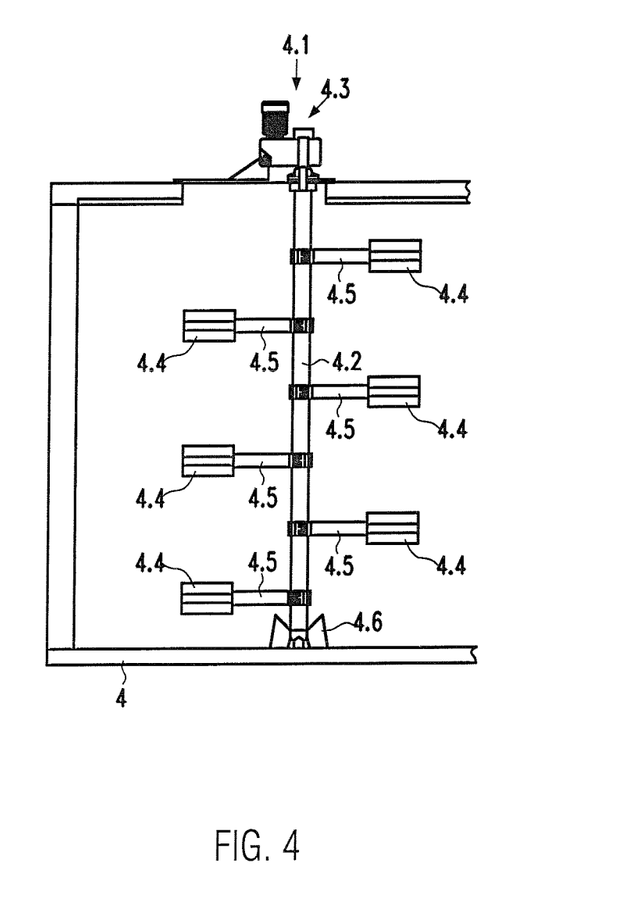

The thick sludge fermenter 4 has an agitator 4.1 for thorough mixing of the reactor content. The agitator 4.1 comprises one or more roughly vertical agitator shafts 4.2 (FIG. 4). Formed at the top end section of the agitator shaft 4.2 is a drive mechanism 4.3. The agitator 4.1 has several paddles 4.4, each fixed to the agitator shaft 4.2 by means of a paddle rod 4.5. The bottom end section of the agitator shaft 4.2 is held by a centring bearing 4.6. The centring bearing 4.6 is located at the base of the thick sludge fermenter 4.

The agitator 4.1 corresponds to the agitator of WO 2007/025739, to which reference is made in this regard.

Via a pipe section 9.14 connected to the pipe section 9.8, a mineral trace element solution can be fed into the thick sludge fermenter 4. Also fed into the thick sludge fermenter can be one of the trace element solutions described above. Preferably the same trace element solution is added to both the thick sludge fermenter 4 and the thin sludge fermenter.

The biogas generated in the thick sludge fermenter 4 flows into the storage tank 5 through a pipe section 9.15 provided at the top end section of the thick sludge fermenter 4.

Provided in the bottom end section of the thick sludge fermenter 4 is a pipe section 9.16 via which the reactor effluent is fed into the storage tank 5.

In the bottom section of the storage tank 5, the reactor effluents from the thin sludge fermenter 3 and the thick sludge fermenter 4 are mixed together. The top section of the storage tank 5 provides for gas storage. The storage tank 5 is preferably a steel or concrete vessel with a double membrane as the tank cover. The double membrane may also be used for gas storage.

Provided at the top of the storage tank 5 is a pipe section 9.17 which leads into a process water tank 14.

Located at the inlet of the pipe section 9.17 into the process water tank 14 is a biogas compressor 13. By means of the biogas compressor 13, the biogas is compressed before being injected into the process water tank 14. The process water tank 14 feeds the pipe sections 9.5 and 9.12 with purified process water. The diameter/height ratio of the process water tank 14 is roughly between 1 and 10.

The storage tank 5 is connected via a pipe section 9.18 to the nitrogen sink 6. The nitrogen sink 6 has a digested sludge separation unit 16 and a thickening unit 19 for the separation of nitrogenous compounds.

The pipe section 9.18 leads into the digested sludge separation unit 16, which is in the form of a decanting centrifuge. It is also possible to provide for the digested sludge separation unit 16 to be in the form of a screw press. The digested sludge separation unit 16 has a temperature control unit 16.1 and/or a pressure regulator 16.2.

Via a pipe section 9.19, a separation aid is fed into the digested sludge separation unit 16. The separation aid is a cationic or anionic flocculation aid and/or a polymer and/or $CaCO_3$ and/or a lye, preferably NaOH, and/or air and/or steam.

In the digested sludge separation unit 16, gaseous nitrogenous compounds are separated from the reactor effluents and the digested sludge. The remaining portion of the digested sludge is split up into a solid digested sludge fraction and a liquid digested sludge fraction in the digested sludge separation unit 16.

The solid fraction may be used as solid fertiliser and is fed via a pipe section 9.20 into a solid fertiliser store 17.

The digested sludge separation unit 16 is connected to a flash boiler 18 via a pipe section 9.21. The liquid fraction from the digested sludge separation unit 16 is transferred into the flash boiler 18 via the pipe section 9.21. A discharge agent is fed into the flash boiler 18 via a pipe section 9.22. In the flash boiler 18, acid gas is driven out of the liquid fraction. The acid gas is e.g. $CO_2$ and/or $H_2S$. This acid gas flow is fed, through a pipe section 9.23 connected to the top of the storage tank, into the top of the storage tank 5, where it mixes with the biogas produced in the fermenters 3, 4.

Via a pipe section 9.24, the flash boiler 18 is connected to a thickening unit. The remaining portion of the liquid fraction enters the thickening unit 19 through pipe section 9.24. In the thickening unit 19, a purified process water flow is separated from the liquid fraction, e.g. by a membrane. The liquid fraction is used as liquid fertiliser. The liquid fertiliser is fed into a liquid fertiliser storage tank 21 via a pipe section 9.25.

The purified process water flow from the thickening unit 19 is transferred into the process water tank 14 through a pipe section 9.26. Via a pipe section 9.27 branching off from the pipe section 9.26, part of the purified process water is fed to the bioethanol plant 1. The pipe sections 9.26 and 9.27 form the process water return flow system 7.

Through a pipe section 9.28, in which is integrated a second compressor 22, the nitrogenous gaseous compounds from the digested sludge separation unit 16 are transferred into pipe section 9.25 where they enrich the liquid fertiliser before the latter is fed into the liquid fertiliser storage tank 21.

The biogas fed into the process water tank 14 is purified and cooled in the process water tank 14. The purified and cooled biogas is withdrawn from the upper section of the process water tank 14 and fed to a biogas recycling unit 8 through a pipe section 9.29.

The biogas recycling unit 8 may be a combined heat and power plant and/or a purification and/or compression stage. The energy obtained by this means is used to operate the upstream bioethanol plant 1 and the apparatus 25 according to the invention so that they are as far as possible completely self-sufficient in energy terms.

Integrated in pipe section 9.29 is a desulphurisation unit 23, into which leads a pipe section 9.30. Via the pipe section 9.30, a process chemical is fed into the desulphurisation unit to liberate the cooled biogas of hydrogen sulphide before it is fed to the biogas recycling unit 8. The process chemical is preferably hydrogen peroxide ($H_2O_2$), oxygen or air.

The separated sulphur is converted into sulphuric acid and fed, via a pipe section 9.31 connected to pipe section 9.22, into this pipe section 9.22 where it is fed to the flash boiler 18 together with the stripping agent.

The process for the conversion into biogas of fermentation stillage arising as a waste product of ethanol production, using the above apparatus according to the invention, is explained below with the aid of an embodiment.

The fermentation stillage from ethanol production which accumulates sequentially or in batches in the bioethanol plant 1 reaches the buffer tank 10 through pipe section 9.1. In the buffer tank 10, the fermentation stillage is compared and stored. The compared fermentation stillage passes from the buffer tank 10 to the separation unit 2 via pipe section 9.2.

In the separation unit 2, the fermentation stillage is separated into a thin fraction and a thick fraction. The thin fraction contains 0.5% to 2% of substances which can be filtered off and a dry weight content of 5 to 12%. The thin fraction passes through pipe section 9.3 into the thin fraction storage tank 11. In the thin fraction storage tank 11, the fermentation stillage is mixed with a stillage conditioning agent fed in via pipe section 9.4 and a purified process water flow from the process water tank 14, which is fed into the thin fraction storage tank 11 through pipe section 9.5. The enriched and diluted fermentation stillage passes through pipe section 9.6 from the thin fraction storage tank 11 into the thin sludge fermenter 3.

The amount of process water added to the thin fraction storage tank 11 is set so that an NH$_4$—N concentration of 8 g/l and/or a substance concentration of 15 g/l which may be filtered off is not exceeded.

The separation of the fermentation stillage in the separation unit 2 is effected in a single stage and without the addition of flocculation aids. The heavy-duty biogas reactor or thin sludge fermenter 3 used here is able to process a certain proportion of substances which may be filtered off. The separation of the fermentation stillage need not therefore be so perfect that a thin fraction completely free from solids is obtained, as would be necessary if a fixed bed biogas reactor were to be used. In the process known from EP 1 790 732 A1, a two-stage separation is carried out, with the addition of a flocculation aid. Here it is true that a better separation result is obtained, but the operating costs are considerably higher due to the addition of the flocculation aid. As heavy-duty biogas reactors, generally fixed-bed biogas reactors are used. In these, the microbiology is installed in a kind of filter, through which the reactor contents must flow. If the reactor contents still include solids, these would settle in the filter, which would become blocked in time. The thin sludge fermenter 3 used in the present embodiment is free of pores and has no such filter, so that a certain proportion of substances able to be filtered off may also be processed in it. The combination of the simple single-stage separation unit 2 and the present thin sludge fermenter 3 is on the one hand very efficient and on the other hand very simple and cost-effective. This represents a considerable advance over conventional comparable plants.

Figure 2:
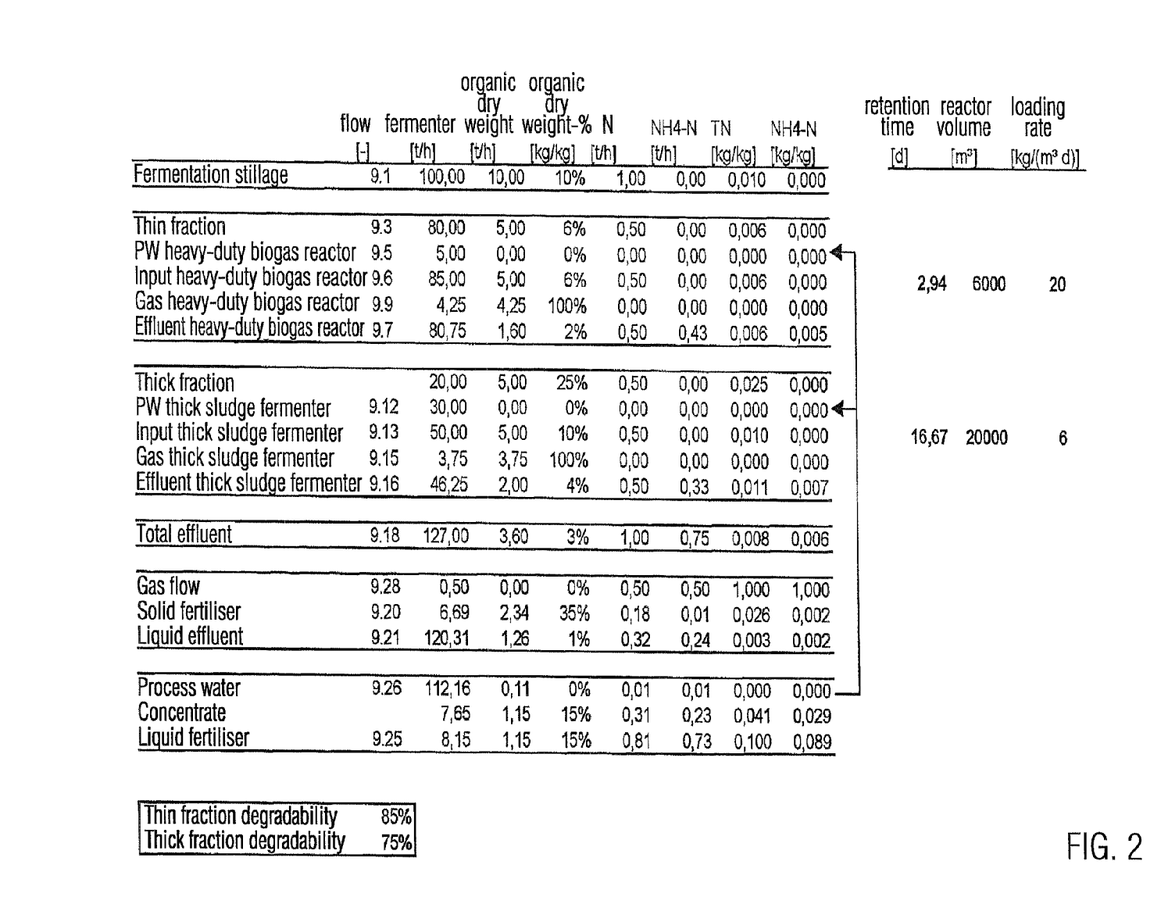

In the present embodiment, in accordance with the mass balance illustrated in FIG. 2, a fermentation stillage flow of 100 t/h is used as a basis. The fermentation stillage contains a dry weight content of 10% (10 t/h) and a nitrogen content (N content) of 1% (1 t/h).

The thin fraction contains with 80 t/h a major portion of the water of the fermentation stillage, and with 5 tonnes of dry weight per hour ($t_{oTM}$/h) around half of the solids of the fermentation stillage. The N content is roughly 5 t/h. A process water flow of around 5 t/h is fed into the thin fraction storage tank. The process water flow is largely nitrogen-free with a concentration of ≤100 mg/l.

The fermentation temperature in the thin sludge fermenter 3 lies between 35° C. and 65° C., depending on the temperature of the thin fraction and the required added amount of process water. Since the fermentation stillages develop a temperature of 60° C. to 80° C., temperature regulation to 35° C. is not always advantageous because of the cooling requirement. It is more expedient to regulate the reactor temperature to a mean reactor inflow temperature, which is then held constant. In this way only limited heating/cooling is necessary and a heat exchanger in contact with the thin sludge fermenter 3 may be correspondingly small. Via pipe section 9.8 a mineral trace element solution may be fed into the thin sludge fermenter 3 and mixed with the thin fraction.

The diluted and enriched thin fraction has an organic dry weight content of around 6%. In the thin sludge fermenter 3, the 85 t/h are fermented with an organic loading rate of around 10 kg organic dry weight per cubic meter and day ($kg_{oTM}$/(m$^3$d)) up to 50 $kg_{oTM}$/(m$^3$d). This results in the production of approximately 4.25 t/h of biogas in the thin sludge fermenter 3.

The ammonium/ammonia content (NH$_4$—N content) amounts to a maximum 10 g/l. However a content of no more than 6 g/l is preferred. At this upper limit a pH value of around 8 is to be expected. With values of 6 g/l and/or 6 kg/m$_3$ for ammonium/ammonia content it is certainly possible to operate the thin sludge fermenter 3. But with minor malfunctions, e.g. temporary failure of the reactor temperature control, changes in substrate when the plant is operated in batch mode, interruption of reactor circulation, etc., the reactor may acidify more rapidly. Acidification in this case means the accumulation of acetic acid, propyl and/or butyric acid with inhibition of the methane producers.

With a loading rate of 20 $kg_{oTM}$/(m$^3$d), the hydraulic retention time in the thin sludge fermenter is 2.9 days. In the present embodiment, the reactor volume of the thin sludge fermenter 3 is around 6000 m$^3$.

The reactor effluent from the thin sludge fermenter 3 passes into the storage tank 5 via a pipe section 9.7. The reactor effluent is roughly 80.75 t/h with an organic dry weight (oTM) content of around 2% (1.6 t/h). The reactor effluent contains virtually all the nitrogen from the fermentation stillage (0.5 t/h).

In the gas collecting spaces 3.4 of the thin sludge fermenter 3, the biogas rising from the respective reactor zones 3.2 located below is impounded. If all of the biogas collected is withdrawn from a gas collecting space 3.4 via a valve 3.5, then a low-gas zone which encourages the sedimentation of biogas develops above a separating element 3.1. If the valve 3.5 is closed, biogas flows over an outer overflow edge 3.6 of the separating element 3.1 through an area of the next reactor zone 3.2 lying above. Since the overflowing biogas rises on one side only into one half of the space, a circulating flow occurs which promotes thorough mixing. The rate of the circulating flow increases as the gas volume flow rises. Through the removal of different volumes of gas flow by adjustment of the valves 3.5, the circulating flow may be set in such a way that on the one hand adequate mixing is obtained and on the other hand the discharge of active biomass is avoided. This results in good mixing in the thin sludge fermenter 3 and adequate retention of active biomass.

In the solids separator, the hydrostatic pressure of the water columns in the pipe section 9.7 is utilised to separate active biomass from the reactor effluent. Because of the associated rise in pressure in the solids separator, dissolved biogas remains in solution, so that sedimentation of the biomass can occur. The active biomass is fed back into the thin sludge fermenter 3 through pipe section 3.9. In this way, washing out of the methanogen and acetogen biomass is prevented despite the low hydraulic retention time in the thin sludge fermenter 3.

In the thin sludge fermenter 3, 4.25 t/h of biogas are produced. The biogas produced passes into a storage tank 5 via a pipe section 9.9. The remaining fermentation stillage or reactor effluent (80.75 t/h) is also fed into the storage tank 5 through pipe section 9.7.

The thick fraction separated in the separation unit 2 contains an organic dry weight content of 20% to 35%. In the present embodiment the organic dry weight content is around 25%. The concentration of the substances which may be filtered off is roughly 15% to 30%. The N content is around 5 t/h.

The thick fraction passes through pipe section 9.10 into the thick fraction storage tank 12. Around 30 t/h of process water are fed into the thick fraction storage tank over pipe section 9.12. Stillage conditioning agent is fed into the thick fraction storage tank through pipe section 9.11. The dry weight content in the thick fraction storage tank 12 is set at approximately 12% to 30%. The diluted and enriched thick fraction passes through a pipe section 9.13 into the thick sludge fermenter 4. The highest possible dry weight content is preferred, since then the thick sludge fermenter 4 may be kept relatively small, and little process water is needed. A high dry weight content may be set, in particular if the thick fraction is low in nitrogen. Biogas reactors which may be operated with a high solids concentration are described for example in DE 103 21 607 A1 and WO 2007/025739, to which reference is made here.

The thick fraction flow amounts to 20 t/h. With 5 $t_{oTM}$/h it contains as much dry weight as the thin fraction flow. The dry weight in the thick fraction is comprised largely of substances which can be filtered off, which are more difficult to decompose than the soluble solid components in the thin fraction. In the thick fraction storage tank 12, 30 t/h of process water is added to the thick fraction, which is diluted only to an organic dry weight content of 10%. In this way the nitrogen concentrations in the thick fraction are also diluted from 25 kg/m$^3$ to 10 kg/m$^3$.

Around 50 t/h of diluted thick fraction are fed into the thick sludge fermenter. The thick sludge fermenter 4 is operated at a loading rate of from 6 $kg_{oTM}/(m^3d)$ to 18 $kg_{oTM}/(m^3d)$. A mineral trace element solution may be added to the thick sludge fermenter 4 via pipe section 9.14. The fermentation temperature in the thick sludge fermenter is set at a constant value between 35° C. and 65° C. As in the thin sludge fermenter 3, the temperature is independent of the temperature of the fraction and the amount of added process water required.

In the thick sludge fermenter 4, the organic dry weight concentration is 4%. The NH$_4$—N concentration comes to 7 kg/m$^3$. With a loading rate of 6 $kg_{oTM}/(m^3d)$, the retention time is approximately 16.7 days. The reactor volume of the thick sludge fermenter in the present embodiment is around 20,000 m$^3$.

In the thick sludge fermenter 4, roughly 3.75 t/h of biogas are produced. The reactor effluent amounts to around 46.25 t/h, including an N content of approximately 5 t/h.

The reactor content of the thick sludge fermenter 4 is continuously circulated through rotation by the agitator 4.1. The biogas produced during fermentation collects below the roof of the thick sludge fermenter 4.

Via the pipe section 9.15 connected in the top section of the thick sludge fermenter 4, the biogas generated in the thin sludge fermenter 4 passes into the storage tank 5.

The reactor effluent from the thin sludge fermenter 3 and the thick sludge fermenter 4 are mixed together in the storage tank 5. The resultant reactor effluent or digested sludge is around 127 t/h, with an organic dry weight content of 3%. The nitrogen content is around 1 t/h.

Approximately 8 t/h of biogas are produced in the thin sludge fermenter 3 and the thick sludge fermenter 4. The biogas is collected in the head space of the storage tank 5 where it is mixed with acid gas from the nitrogen sink 6.

The reactor effluent or digested sludge from the storage tank 5 is fed via pipe section 9.18 to the digested sludge separation unit 16. In addition, a separation aid is fed into the digested sludge separation unit 16 through pipe section 9.19. The addition of the separation aid improves the separation properties of the digested sludge separation unit. The nitrogenous gases released during separation, in particular NH$_3$, are carried off through pipe section 9.28.

The separation of the digested sludge into a liquid fraction, a solid fraction and gases in the digested sludge separation unit 16 improves with higher temperature and pH value, and with stronger gas flow from the digested sludge separation unit 16.

The removed gaseous flow is compressed in the compressor 20 which is integrated in pipe section 9.28. The volumetric flow of the gas may be adjusted via the output of the compressor 20 and the temperature set in the digested sludge separation unit 16. Provision may also be made to inject air and/or steam into the digested sludge separation unit 16, to adjust the gas flow in this manner.

In this way the digested sludge separation unit 16 in the form of a centrifuge performs two functions, the separation of the solids from the liquid, and the separation of the liquid from the gas. To assist in the separation of the solids from the liquid, preferably cationic flocculation aids are added. These neutralise the surface charge of the pellets which form during centrifuging, thereby improving the solid/liquid separation properties. Iron and aluminium salts, calcium carbonate and/or polymers may be used as flocculation aids. To assist the gas/liquid separation, a gas flow of air or water vapour may be added as a separation aid. Since the pressure is lowered by the compressor 20 in the digested sludge separation unit 16, the liquid in the digested sludge separation unit 16 boils at quite low temperatures, by which means all dissolved gases (CO$_2$, H$_2$S, NH$_3$) are degassed. Depending on the proportions of the dissolved gases it may be sensible to raise or lower the pH value. With a higher pH value, the NH$_3$/NH$_4^+$ balance shifts towards the volatile NH$_3$ component. With this digested sludge separation unit 16 it is therefore possible to separate the individual phases—solid, liquid and gaseous—from one another very efficiently, while at the same time the stripping out of ammonia may be set specifically.

In the prior art there are a number of attempts to strip out ammonia. However these could not be realised in practice since they would have required either too much energy and/or too much separation aid, in particular NaOH, both of which would have led to a considerable increase in processing costs. The process here differs from the corresponding processes in the prior art in that:

1. large amounts of acid gases (CO$_2$, H$_2$S) are dissolved which in the stripping out of gases generate an auxiliary flow which assist the stripping out of ammonia. This auxiliary flow is already present and does not need to be added.

2. the removal of the acid gases raises the pH value, shifting the balance towards ammonia.

3. in the present process there is a greater amount of low-temperature waste heat, with a temperature too low for heating the reactors. This low-temperature waste heat is however highly suitable for heating the digested sludge and in this way assisting the stripping out of ammonia.

In the process described here it is not necessary to supply energy from the outside. Moreover, small amounts of separation aid (NaOH) are sufficient to set the pH value correctly.

The solid portion of the digested sludge or the solid fraction amounts to roughly 6.7 t/h and has an organic dry weight content of 25% to 45%, preferably around 35%. The solid fraction is used as solid fertiliser. The solid fertiliser reaches the solid fertiliser store 17 via a pipe section 9.29. The solid fertiliser is produced at around 6/7 t/h with an N content of roughly 0.18 t/h.

The major portion of the digested sludge, the liquid fraction, in the present embodiment 120.31 t/h, is fed into a flash boiler 18 via a pipe section 9.21. This liquid flow has an organic dry weight content of 1.0%. The temperature and pressure of the flash boiler 18 are regulated by a temperature controller 16.1 and a pressure regulator 16.2. In the flash boiler 18 the liquid portion is provided with a stripping agent and dilute sulphuric acid through a pipe section 9.22. This acidification effects a partial stripping out of the dissolved acid gases CO$_2$ and H$_2$S. The acid gases are removed from the flash boiler via a pipe section 9.23 and fed into the head space of the storage tank 5, where they mix with the biogas produced in the fermentors 3, 4. Preferably H$_2$SO$_4$ is used as acidification agent.

Through the addition of the acid gas to the biogas, it is burned in the combined heat and power plant together with the rest of the biogas, and escapes to the environment mainly in the form of $CO_2$. Before combustion, the acid gas is desulphurised together with the biogas. This is explained in detail below. Alternatively the acid gas could also be specially treated. However this incurs considerable costs and does not give any different result.

The temperature in the flash boiler 18 should be as high as possible to obtain optimal separation. Sulphuric acid is added with control of the pH value. The pH value in the flash boiler should be reduced to less than 5. Any further lowering of the pH value brings about no noticeable improvement in separation. The amount of gas stripped out no longer increases noticeably, only the acid consumption rises. If the mass transfer of the dissolved gas from the liquid into the gaseous phase is limited, then the addition of an enzyme preparation with carboanhydrase activity such as e.g. carboanhydrase can lead to improved outgassing. The enzyme preparation prevents local $CO_2$ oversaturation, which would suddenly outgas spontaneously. While purified carboanhydrase is very expensive, it often occurs in the purification of proteins in waste fractions with high carboanhydrase activity. Preferably such waste fractions are fed to the flash boiler 18. Only a small amount of carboanhydrase (e.g. a few μg) are enough to bring several cubic meters of supersaturated $CO_2$ solution back into equilibrium. Alternatively, agitators or other gas liquid exchange elements could be installed to improve outgassing. In this way it is possible to keep the size of the flash boiler to a minimum.

The degassed liquid discharge and/or the liquid fraction from the flash boiler 18 pass through pipe section 9.24 to a thickening unit 19. Integrated in pipe section 9.24 is a compressor 20 or a conveyor/pressure raising unit. In this way the remaining liquid fraction is conveyed to the thickening unit 19.

In the thickening unit 19, 112.2 t/h of purified low-nitrogen process water with an organic dry weight content of around 0.1% are produced. Via a pipe section 9.26, 35 t/h of this process water reach the process water tank 14, from which they are fed via pipe section 9.12 to the thick fraction storage tank 12, and over pipe section 9.5 to the thin fraction storage tank for nitrogen dilution. The rest passes through pipe section 9.27 to the bioethanol plant 1, where it is used for mashing.

In the thickening unit 19, after separation of the process water, there is a liquid fraction of roughly 7.65 t/h, which is concentrated to a dry weight content of 10% to 20% and preferably 15%. The process water flow from the thickening unit 19 has a dry weight content of 0% to 1%. The liquid fraction may be used as liquid fertiliser and passes via pipe section 9.25 into the liquid fertiliser tank 21. In pipe section 9.25 the liquid fertiliser is enriched via pipe section 9.28 with the nitrogenous gases from the digested sludge separation unit, in particular with ammonia ($NH_3$). This increases the nutrient content of the liquid fertiliser. The liquid fertiliser produced contains 81% of the nitrogen flow fed to the biogas plant 25 via the fermentation stillage. Of this, 90% is in the form of bio-available ammonium. The low pH value of the liquid fertiliser ensures low volatility of the ammonium in application of the liquid fertiliser, since the dissociation balance is shifted to the side of the non-volatile ammonium ion ($(NH_4^+)$).

The biogas produced in the thin sludge fermenter 3 and the thick sludge fermenter 4 is routed through the head space of the storage tank 5. Via pipe section 9.23, the acid gas from the flash boiler 18 also enters the head space of the storage tank 5, where both gases are mixed together.

Through pipe section 9.17, the biogas passes to the biogas compressor 13. In the biogas compressor 13 the biogas is compressed to e.g. 0.3 bar and fed to the liquid phase of the process water tank 14 via a freely distributed nozzle injection system. The pressure generated by the biogas compressor 13 corresponds to the pressure exerted by the water column in the process water tank 14. In this way the biogas is dried and cooled. The dry mass flow amounts to around 8 t/h. The composition of the dry biogas is approximately 60% methane and 40% carbon dioxide. The process water tank 14 is designed so that the gassing rate is preferably 0.1 vvm to 0.2 vvm (1 vvm=1 volume gas per volume liquid per minute). With the feeding of biogas at 55° C. into process water at 20° C., a reduction in water vapour content of almost 80% is obtained. At the same time the process water heats up by around 3° C. The pH value falls due to the partial dissolving of $CO_2$ and $H_2S$ in the process water. Traces of ammonia still present in the biogas dissolve almost completely in the process water with an acid pH value. A subsequent ammonia wash is therefore not required.

The cooled biogas passes through pipe section 9.29 to the biogas desulphurisation unit 23. A process chemical is fed into the desulphurisation unit 23 via pipe section 30. In the desulphurisation unit 23, the sulphur content of the biogas is reduced from around 5,000 to 20,000 ppm (parts per million) to around 100 ppm. Desulphurisation is effected through an $H_2O_2$ contraflow. The resulting sulphuric acid flow amounts to 0.42 t/h $H_2SO_4$ in aqueous solution. Through pipe section 9.31 the sulphuric acid flow arrives at pipe section 9.22, where it is mixed with the stripping agent and fed to the flash boiler 18.

The desulphurised biogas flow may now be recycled for its energy and arrives at the biogas recycling unit 8 via pipe section 9.29. Here the desulphurised biogas is fed either to a combined heat and power plant or a burner or a combination of the two, to meet the energy requirements of the bioethanol plant 1 and/or the biogas plant 25. It is also possible to feed the biogas to a purification and compression stage, for feeding into a local gas network.

In a simplified embodiment, a conventional reactor may be used instead of the heavy-duty biogas reactor.

Depending on demand and the size of the plant, several thin sludge fermenters and thick sludge fermenters may also be provided.

The biogas plant may also be designed without a nitrogen sink, but in this case it is not possible to recirculate the process water.

Due to the fact that the fermentation stillage is split into a thin fraction and a thick fraction, the thin fraction may be fermented independently of the thick fraction. The thin fraction contains a high proportion of soluble solids and either no or else a very low proportion of insoluble solids. Through the provision of two reactors, which are individually geared to their content, the thin fraction may be processed with a high throughput, and the thick fraction independently of the former with the necessary retention time and correspondingly lower throughput. Since the thin fraction is converted into biogas very rapidly in the heavy-duty biogas reactor, a reactor with very low volume is adequate. This reduces the energy required to control the reactor temperature and makes the whole process very efficient in energy terms. Moreover, in comparison with conventional apparatus, an altogether smaller reactor volume is needed for the same throughput. The smaller reactor sizes reduce surface area and therefore heat loss. In addition, the thermal power required to regulate the bioreactor to a predetermined temperature is significantly less. Preferably the reactor temperature is set so as to be just above the maximum temperature of the reactor inflow. The temperature of the reactor inflow is somewhat lower in winter than in the summer. By setting the target temperature to a value just above the maximum temperature of the reactor inflow, the temperature in the reactor may be kept at the target temperature solely by heating. It is then not necessary to provided cooling equipment.

In the nitrogen sink, a low-nitrogen process water flow is produced from the reactor effluent. Because of this it is possible to return the low-nitrogen process water flow to the biogas reactor, in order to dilute the fermentation without at the same time raising its pH value. On the one hand this saves the cost of fresh process water while on the other hand avoiding the concentration of too much ammonia in the reactor, since ammonia is toxic to the micro-organisms in the reactor. In addition the loading rate may be higher than with the prior art, since the biogas reactor operates more efficiently. It is therefore possible to provide a lower reactor volume. This reduces the energy needed for regulating the biogas reactor temperature, and makes the whole process highly efficient in terms of energy. In comparison with conventional apparatus, an altogether smaller reactor volume is needed for the same throughput. A further benefit of the process water recovery is that the amount of effluent for disposal is reduced, and the concentration of fertiliser in the effluent flow rises and less water needs to be moved.

Due to the high loading rates and the ability to dispense with diluted CO substrate with low methane yield, the heat requirement of the biogas plant is so low that the biogas flow occurring is sufficient to cover the heat and electrical energy needs of the biogas and bioethanol plants. As compared with the prior art, the apparatus according to the invention requires only less than half the reactor volume for the same quantity of fermentation stillage. Through the incorporation of nitrogen sinks in the digested sludge separation and the thickening, a low-nitrogen process water flow is produced. Because of the nitrogen dilution by process water in the fermenters, and the separation of the substances which may be filtered off, even in the thick sludge fermenter a higher loading rate may be applied than in fermenters known from the prior art.

The figures quoted in the description of the embodiment are shown in the form of a summary mass balance table in FIG. 2. They represent a possible, realistic example. In FIG. 2, FM stands for fermenter, HRT for retention time, VR for reactor volume and BV for loading rate. All percentages in the above description of the invention are percentages by weight. Within the scope of the invention it is however also possible to scale the apparatus up or down, so that the individual masses and flows may assume different values.

In another embodiment of the invention the thin fraction obtained after the single-stage separation is subjected to an anaerobic digestion in a thin sludge biogas fermenter, while the thick fraction is used as solid fertiliser, either with or without further processing. Such a process comprises the steps of a single-stage separation unit, a heavy-duty biogas reactor and, optionally, a nitrogen sink as described above, but not an anaerobic digestion of the thick fraction. Preferably, the thin sludge biogas fermenter is a heavy-duty biogas fermenter with, most preferred, a pore-free flow path.

EXAMPLE

Fermentation of Thin Wheat Stillage in a 9 m³ Pilot Plant

Figure 5:
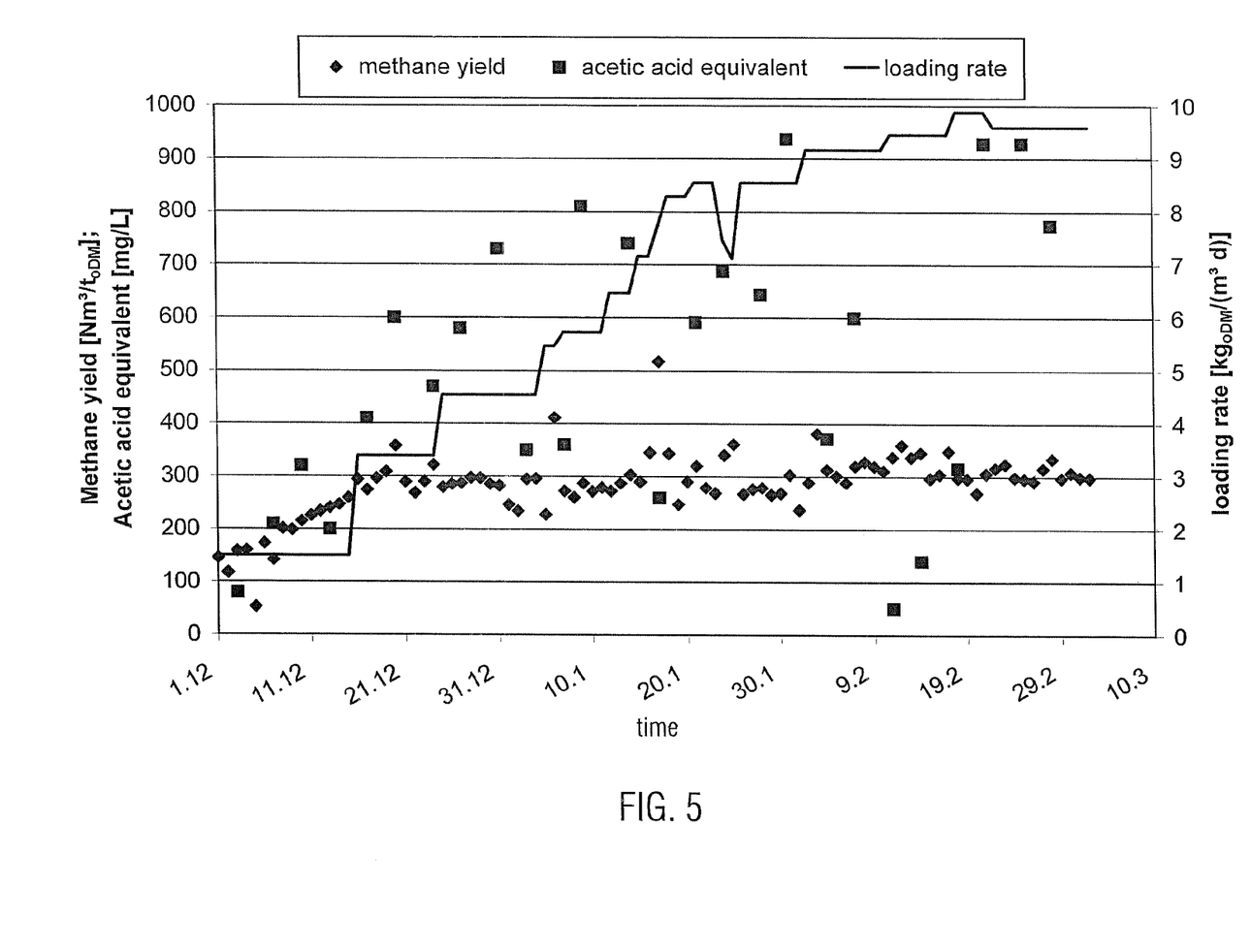
Figure 6:
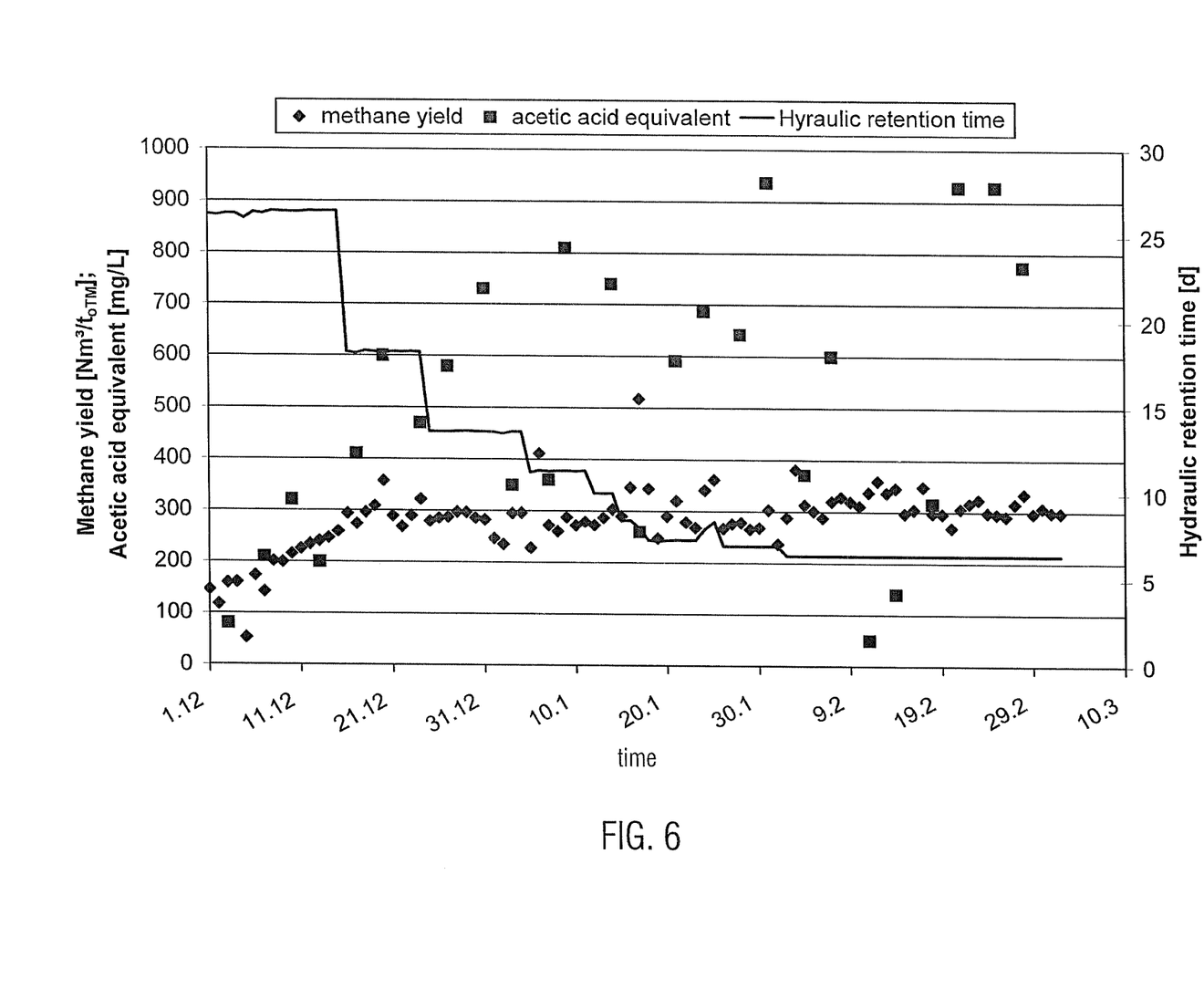
FIG. 6 a diagram of the fermentation of FIG. 5 showing the methane yield, acetic acid equivalent and loading rate and hydraulic retention time.

After decanting thin wheat stillage having an organic dry weight content of 7% is digested without any further treatment in a 9 m³ stirred-tank reactor which is equipped with a biomass retention according to DE 100 05 114 A1 and EP 1 134 194 B1. These documents are incorporated herein by reference. The fermentation is carried out with a hydraulic retention time of 6 days at a loading rate of 10 $kg_{oTM}/(m^3 d)$, whereas the methane yield keeps stable also at high loading rates and the acetic acid equivalent remains under 1 g/L. The data is shown in FIGS. 5 and 6 (the experiment was stopped due to the consumption of the substrate).

| List of reference numbers | |
|---|---|
| 1 | bioethanol plant |
| 2 | separation unit |
| 3 | thin sludge fermenter |
| 3.1 | separating elements |
| 3.2 | reactor zone |
| 3.3 | reactor wall |
| 3.4 | gas collecting space |
| 3.5 | valve |
| 3.6 | overflow edge |
| 3.7 | pipe section |
| 3.8 | solids separator |
| 3.9 | pipe section |
| 4 | thick sludge fermenter |
| 4.1 | agitator |
| 4.2 | agitator shaft |
| 4.3 | drive mechanism |
| 4.4 | paddle |
| 4.5 | paddle rod |
| 5 | storage tank |
| 6 | nitrogen sink |
| 7 | process water return pipe |
| 8 | biogas recycling unit |
| 9.1 to 9.31 | pipe section |
| 10 | buffer tank |
| 11 | thin fraction storage tank |
| 12 | thick fraction storage tank |
| 13 | biogas compressor |
| 14 | process water tank |
| 15 | |
| 16 | digested sludge separation unit |
| 16.1 | temperature control |
| 16.2 | pressure regulator |
| 17 | solid fertiliser store |
| 18 | flash boiler |
| 19 | thickening unit |
| 20 | compressor |
| 21 | liquid fertiliser tank |
| 22 | compressor |
| 23 | desulphurisation unit |

The invention claimed is:

1. An apparatus for the conversion into biogas of fermentation stillage arising as a waste product of ethanol production in a bioethanol plant, the apparatus comprising:
    a first separation unit for the separation of the fermentation stillage into a thin fraction and a thick fraction, wherein the thin fraction has a lesser dry weight content than the thick fraction,
    a first biogas reactor downstream from the first separation unit, wherein the first biogas reactor is designed to ferment the thin fraction and is connected to the first separation unit via a pipe for transferring the thin fraction from the first separation unit to the first biogas reactor,
    a second biogas reactor downstream from the first separation unit, wherein the second biogas reactor is designed to ferment the thick fraction and is connected to the first separation unit via a pipe for transferring the thick fraction from the first separation unit to the second biogas reactor,
    a storage tank for collection of biogas produced in the first and second biogas reactors, a second separation unit, in the form of a nitrogen sink, to provide process water low in nitrogen or free from nitrogen from the reactor effluent from the first and second biogas reactors, and a return pipe from the second separation unit in the form of a nitrogen sink into the bioethanol plant, to return the effluent process water for dilution of the reactor content in the biogas reactors.

2. The apparatus according to claim 1, wherein the second separation unit has a decanting centrifuge or a membrane filter unit, a drum filter and/or a drum screen.

3. The apparatus according to claim 1, wherein the first biogas reactor is a heavy-duty biogas reactor.

4. The apparatus according to claim 1, wherein the first biogas reactor has a reactor vessel and a solids separator downstream of the reactor vessel to which the reactor effluent of the reactor vessel is fed, wherein the solids separator is so designed that the reactor effluent in the solids separator is put under pressure so that the expulsion of gases is minimized and solids may settle, wherein there is provided between the solids separator and the reactor vessel a pipe section to return the solids settling in the solids separator to the reactor housing.

5. The apparatus according to claim 1, wherein a pipe section is provided between the reactor vessel and the solids separator to feed the reactor effluent to the solids separator, wherein the solids separator is mounted below the connection point of pipe section to the reactor vessel so that a hydrostatic pressure develops in pipe section and pressurizes the reactor effluent in the solids separator.

6. The apparatus according to claim 1, wherein the first biogas reactor has separating elements which define gas collecting spaces, open downwards and arranged one above the other inside the first biogas reactor, wherein each of the separating elements has an overflow edge, over which volume-controlled biogas may flow into a reactor zone above the separating element in such a way that a defined circulating flow may be set in this reactor zone.

7. The apparatus according to claim 1, wherein the second biogas reactor includes at least one of a hydraulic circulation, an agitator and a gas circulation.

8. The apparatus according to claim 1, wherein a storage tank for the thick fraction is provided between the separation unit and the second biogas reactor.

9. The apparatus according to claim 1, wherein a storage tank for the thin fraction is provided between the separation unit and the first biogas reactor.

10. The apparatus according to claim 1, wherein the first biogas reactor and the second biogas reactor have outlets which lead into the storage tank, wherein the reactor effluents from the first biogas reactor and the second biogas reactor are mixed together in the storage tank.

11. The apparatus according to claim 1, wherein the storage tank has a head space which is designed as a gas reservoir.

12. The apparatus according to claim 1, wherein the apparatus has a digested sludge separation unit to separate gaseous nitrogenous compounds from the reactor effluents.

13. The apparatus according to claim 12, wherein the digested sludge separation unit is a decanting centrifuge or a screw press.

14. The apparatus according to claim 12, wherein the digested sludge separation unit has at least one of a temperature regulator and a pressure regulator.

15. The apparatus according to claim 12, wherein the digested sludge separation unit has a downstream flash boiler for the stripping out of gases and the flash boiler is connected with the storage tank by a pipe for piping the stripped out gases to the storage tank.

16. The apparatus according to claim 15, wherein a thickening unit is provided downstream of the flash boiler.

17. The apparatus according to claim 16, wherein the thickening unit is an evaporation unit or a membrane separation unit.

18. The apparatus according to claim 1, wherein the apparatus has a solid fertilizer store.

19. The apparatus according to claim 1, wherein the apparatus has a liquid fertilizer tank.

20. The apparatus according to claim 1, wherein the apparatus has a process water tank for supplying the biogas reactors with process water.

21. The apparatus according to claim 10, wherein upstream of the process water tank is a biogas compressor, wherein the biogas compressor compresses the biogas so that it may be injected into the process water tank.

22. The apparatus according to claim 1, wherein the apparatus has a desulfurization unit designed to desulfurize the biogas.

23. The apparatus according to claim 1, wherein the apparatus has a unit for recycling the biogas for energy purposes.

24. The apparatus according to claim 23, wherein the unit for recycling for energy purposes is one of (a) a burner and (b) a combined heat and power plant.

25. The apparatus according to claim 24, wherein the combined heat and power plant has a gas turbine and a generator.

26. The apparatus according to claim 1, wherein the apparatus has a purification unit to purify the biogas and a compression stage to feed the biogas into a gas network.

27. The apparatus according to claim 26, wherein the purification unit to purify the biogas is a gas permeation unit.

28. The apparatus according to claim 1, wherein the first separation unit is designed with a single separation stage unit and the first biogas reactor is a biogas reactor through which the thin fraction flows, while the flow path in the biogas reactor is pore-free so that the thin fraction may be fermented in the biogas reactor with a low proportion of solids.

29. The apparatus according to claim 1, wherein the first separation unit separates the fermentation stillage into a thin fraction and a thick fraction, wherein the thin fraction has a dry weight content of total solids up to about 20%.

30. The apparatus according to claim 29, wherein the first separation unit separates the fermentation stillage into a thin fraction and a thick fraction, wherein the thick fraction has a dry weight content of about 20 to about 40%.

* * * * *